(12) United States Patent
Narayan et al.

(10) Patent No.: US 7,456,265 B2
(45) Date of Patent: Nov. 25, 2008

(54) CARBOXYLATED POLYSACCHARIDES AND METHOD OF PREPARATION AND USE

(75) Inventors: Ramani Narayan, Okemos, MI (US); Laura M. Fisher, Dearborn, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 457 days.

(21) Appl. No.: 11/125,865

(22) Filed: May 10, 2005

(65) Prior Publication Data

US 2005/0249778 A1 Nov. 10, 2005

Related U.S. Application Data

(60) Provisional application No. 60/569,723, filed on May 10, 2004.

(51) Int. Cl.
*C07H 1/00* (2006.01)
*C08B 31/18* (2006.01)
*C08B 33/08* (2006.01)
*C08B 35/08* (2006.01)
*C08B 1/00* (2006.01)

(52) U.S. Cl. .......................... 536/1.11; 536/105; 536/56

(58) Field of Classification Search ....................... None
See application file for complete search history.

(56) References Cited

U.S. PATENT DOCUMENTS 2,894,945 A * 7/1959 Hofreiter et al. ............ 536/105
6,811,996 B1 * 11/2004 Inoue et al. ................... 435/24

FOREIGN PATENT DOCUMENTS

WO         WO 9507303 A1 *  3/1995

* cited by examiner

*Primary Examiner*—Shaojia Anna Jiang
*Assistant Examiner*—Layla Bland
(74) *Attorney, Agent, or Firm*—Ian C. McLeod; Steven M. Parks

(57) ABSTRACT

Chemically modified dicarboxy polysaccharides are described. The modified polysaccharides are useful as a carrier for cosmetics, pharmaceuticals, veterinary products and the like. The modified polysaccharides can provide a timed release of active ingredients.

6 Claims, 13 Drawing Sheets

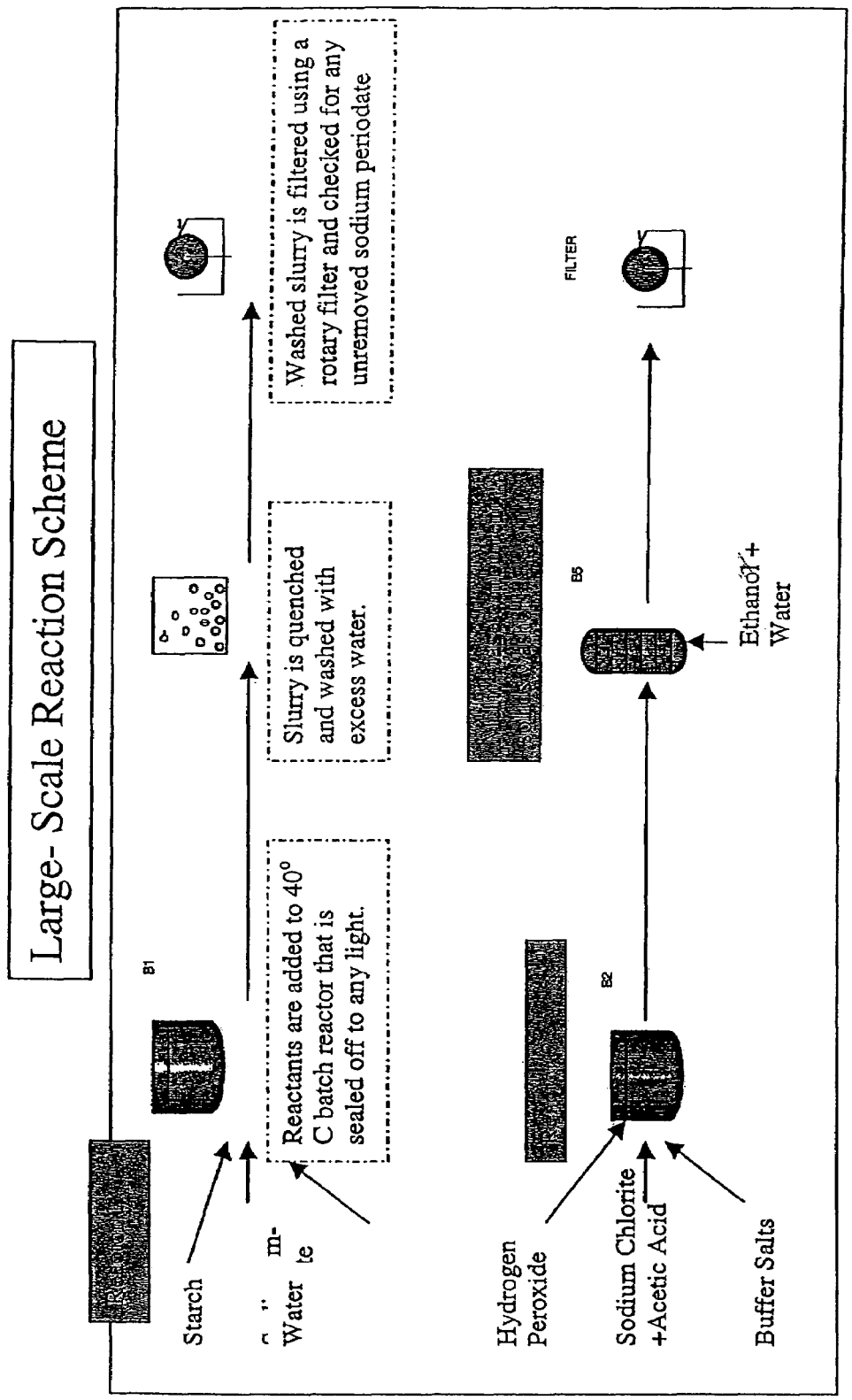
Figure 40. Large-scale reaction scheme

CARBOXYLATED POLYSACCHARIDES AND METHOD OF PREPARATION AND USE

CROSS-REFERENCE TO RELATED APPLICATIONS

This application relies for priority on U.S. provisional application Ser. No. 60/569,723, filed May 10, 2004.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to the preparation of chemically modified polysaccharides which have carboxylic acid moieties and which are water dispersible and useful as carriers. The composition provides a timed release of the chemicals in pharmaceuticals, veterinary medicaments and cosmetics. The present invention also provides a process for the preparation of chemically modified polysaccharides.

(2) Description of the Related Art

The prior art describes various compositions derived from natural carbohydrates for use as carriers and processes for the preparation of modified carbohydrates, particularly cellulose. Natural polymers and gums have been used in pharmaceutical formulations of sustained-release carriers, and modified celluloses, carboxy methylcellulose (CMC) and modified methyl cellulose (MMC) are found in a large number of formulations as viscosity enhancers. Because of their wide acceptance of these modified natural polymers, pharmaceutical companies are interested in the use of modified natural polymers for their drug delivery systems. Natural polymers with gelling properties that have been successfully used in topical formulations include gellan gum and carrageenans. Topical formulations with gelling properties afford increased bioavailability of certain drugs.

OBJECTS

It is an object of the present invention to provide modified polysaccharides for use in cosmetic, medical and veterinary medicinal applications. It is further an object to provide modified polysaccharides which can be produced on a large scale. These and other objects will become increasingly apparent by reference to the following description.

SUMMARY OF INVENTION

The present invention relates to a process for the preparation of carboxylic acid moieties on a chemically modified polysaccharide (CMP) which comprises: selectively oxidizing in an aqueous solution a polysaccharide of linked saccharide rings so that saccharide rings are opened to provide $C_2$ or $C_3$ aldehyde moieties; and selectively oxidizing one or both of the aldehyde moieties to form the carboxylic acid moieties to provide the carboxylic acid moieties on the CMP and wherein the CMP is water dispersible.

Preferably the aldehyde moieties on each opening polysaccharide ring are reduced to a hydroxyl moiety. Preferably both $C_2$ or $C_3$ are carboxylic acid groups.

The present invention also relates to a chemically modified polysaccharide (CMP) comprising linked saccharide rings with ring opened saccharide units at $C_2$ or $C_3$ bond and containing carboxylic acid moieties or water dispersible salt as a random copolymer wherein the CMP is water dispersible to form a clear solution. Preferably one or both of $C_2$ or $C_3$ is a hydroxyl group other than at units which have carboxyl group. Preferably both $C_2$ or $C_3$ are carboxylic acid groups. Preferably the CMP is a copolymer of linked units of the formula:

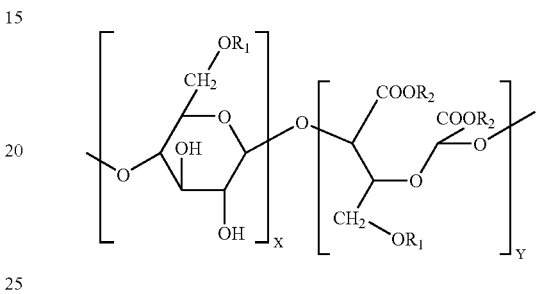

wherein ring opened units in the copolymer are between 10 to 90 mole percent, wherein $R_1$ is H or COOR where R is alkyl or aryl, and wherein $R_2$ is H, alkyl or an aryl group containing 1 to 12 carbon atoms.

The present invention also relates to a pharmaceutical composition which comprises: a medicament; and a chemically modified polysaccharide (CMP) comprising linked saccharide rings with ring opened saccharide units at $C_2$ or $C_3$ bond and containing carboxylic acid moieties or water dispersible salt as a random copolymer wherein the CMP is water dispersible to form a clear solution as a time release adjuvant for the medicament. Preferably the medicament is to be used for treatment of tissue for a living animal. Preferably the medicament is to be used for treatment of tissue of a living human or lower mammal.

The present invention also relates to a method for providing a timed release medicament to a tissue of an animal in need thereof which comprises: providing a composition which comprises: a medicament; and a chemically modified polysaccharide (CMP) comprising linked saccharide rings with ring opened saccharide units at $C_2$ or $C_3$ bond and containing carboxylic acid moieties or water dispersible salt as a random copolymer wherein the CMP is water dispersible to form a clear solution as a time release adjuvant for the medicament; and providing the medicament on the tissue to provide the timed release. Preferably the tissue is of a living animal. Preferably the tissue is of a living human.

Dicarboxy polysaccharides are useful because of their water dispersibility, their mucoadhesive capacity and because their breakdown products are known and safe. Experimental data by Singh et al (Singh, M., et al., Biodegradation Studies on Periodate Oxidized Cellulose. Biomaterials, 3(1): p. 16-20 (1982)) has shown that dicarboxy cellulose matrices are biocompatible and can be broken down in the body by metabolism into 2-carbon and 4-carbon intermediates.

BRIEF DESCRIPTION OF DRAWINGS

FIG. 17 shows large-scale reaction scheme.

DESCRIPTION OF PREFERRED EMBODIMENTS

The present invention provides a flexible, water dispersible, biocompatible material. It was determined that engineering carboxy groups onto a natural polysaccharide backbone was used to provide a water dispersible biocompatible material. Starch and cellulose were chosen as the polysaccharide backbone because of their abundance and their current acceptance in other pharmaceutical applications. The oxidation of starch and cellulose is not a new science, but the application of these oxidized polysaccharides to drug delivery systems is novel. Different methods of oxidation are known, including the use of sodium periodate, hypochlorite, or ozone. All of these methods can be used separately or combined until the desired material properties are achieved. Oxidation by sodium periodate was preferred research because it has the best method to control the position and extent of oxidation.

Figure 1:
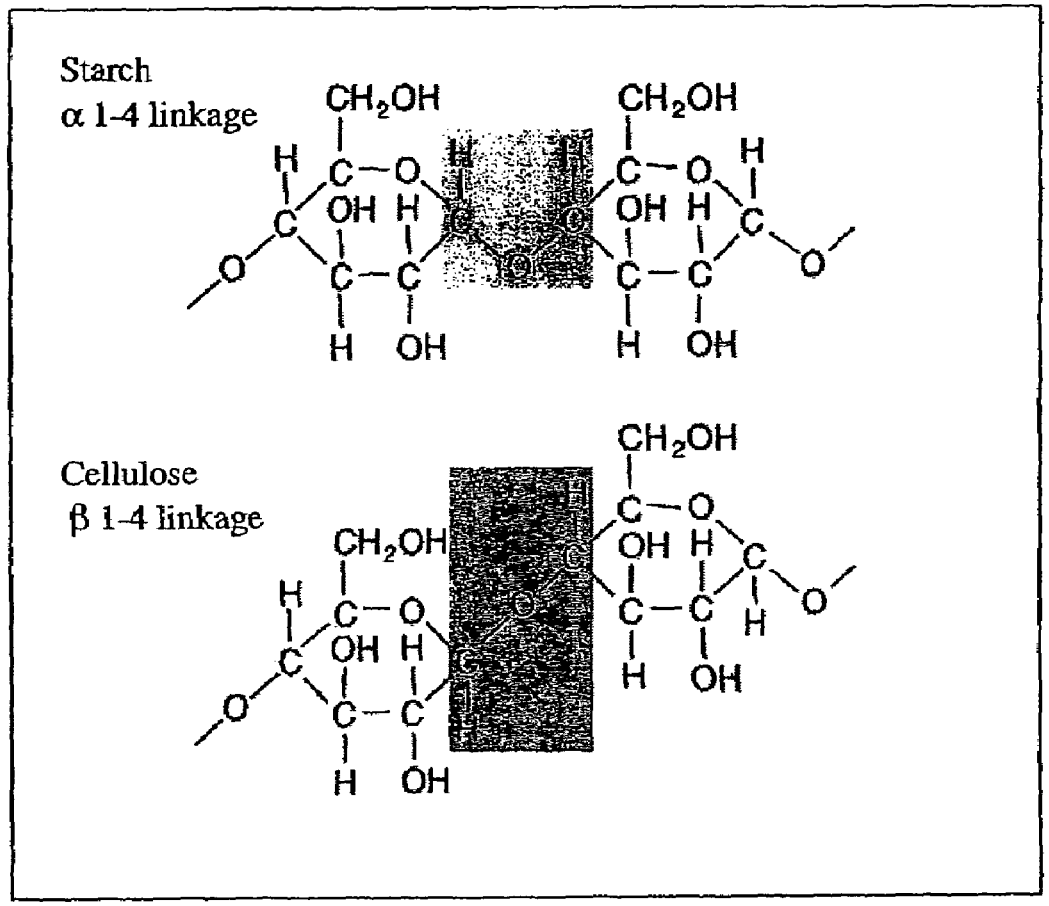
FIG. 1 shows the structures of starch and cellulose.

Cellulose and starch both consist of repeating glucose units with only the glycosidic bond differing as seen in FIG. 1. The oxidation methods can be applied to either structure, although there are differences in the kinetics because of the structure of the materials. Starch is composed of amylase that forms a helical structure. When the material is hydrated the helices open and water can penetrate the material easily. Cellulose, on the other hand, forms a tight crystalline structure that is not as easily hydrated.

Figure 2:
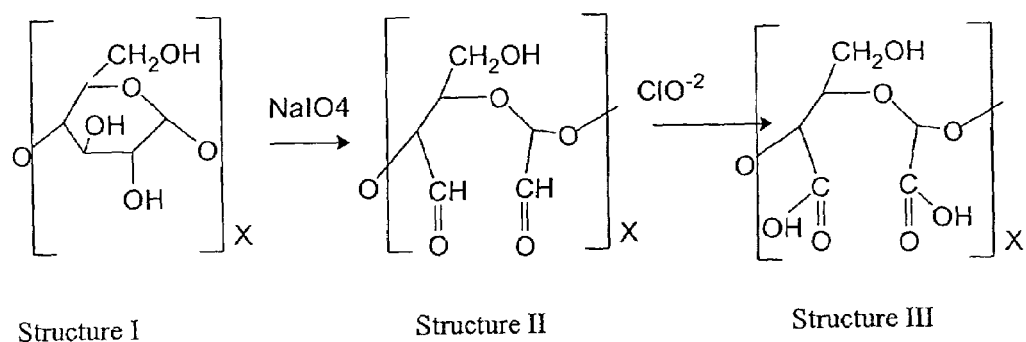
FIG. 2 shows a reaction scheme oxidation of starch.

In the periodate method the starch/cellulose ring is opened between the C-2 and C-3 using $NaIO_4$ in the first step (Floor, M., et al., Preparation and calcium complexation of oxidized polysaccharides. II: Hydrogen peroxide as co-reactant in the chlorite oxidation of dialdehyde glucans. Recl. Trav. Chim. Pays-Bas. 108, 384-392 (1989)) which forms an aldehyde structure. Secondly, the dialdehyde is oxidized using any oxidizing agent (i.e. NaOCl) and carboxyl groups are formed at the C-2 and C-3 (see FIG. 2).

In this method, by controlling the amount of ring opening, the total amount of carboxylation can be controlled. Floor (Floor, et al) described a process where the second step oxidation uses hydrogen peroxide as an inexpensive HOCl scavenger that reduces the HOCl. The reaction is as follows:

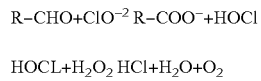

$HOCL+H_2O_2$ $HCl+H_2O+O_2$

This was an important improvement over previous methods which used $ClO^{-2}$ as a scavenger. Besides being less toxic and less expensive, Floor et al reports that this method gives higher yields of the dicarboxy polysaccharide with superior calcium sequestering properties as compared to the reactions using chlorite as the scavenger.

Figure 3:
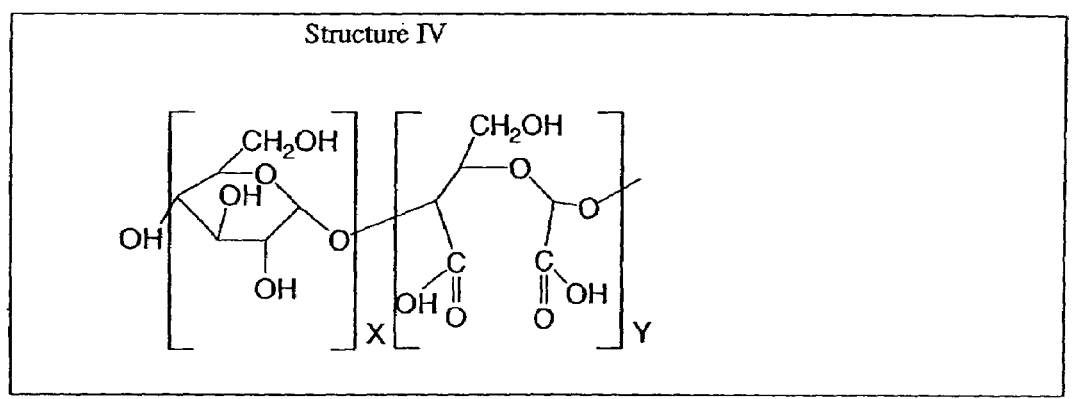
FIG. 3 shows a copolymer starch structure.

By controlling the amount, nature, and conditions of oxidation or hydrolysis, the percent carboxyl groups incorporated, the position of attachment, and the molecular weight are controlled. By effectively controlling the first periodate oxidation step, copolymers can be formed that contain both the structure of the glucose ring and the flexibility of the open ring structure with —COOH groups on them (structure IV), as shown in FIG. 3.

A completely flexible copolymer structure is engineered by partial oxidation of the —CHO groups to —COOH and reducing the remaining aldehyde groups to —OH using sodium borohydride.

Figure 4:
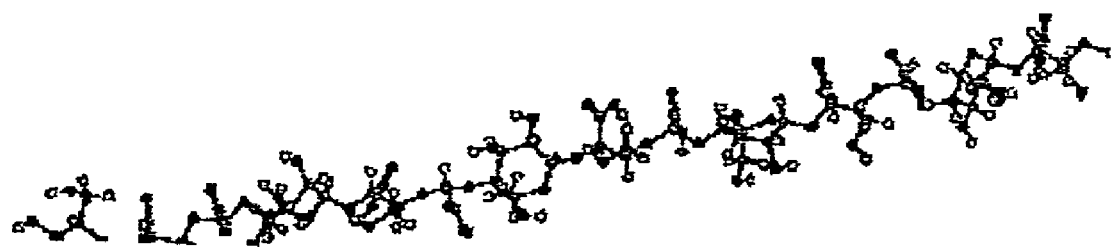
FIG. 4 shows 3D structure of 50% dicarboxy starch.

The dicarboxy polysaccharides are stable at the alkaline pH of the washing process but are degraded under the acidic wastewater (pH 4-5) conditions due to their polyacetal structure. The resulting mono- and oligomeric fragments are readily biodegradable but will not form the structure needed for this application. Floor (Floor, et al) shows that at a pH=3 the dicarboxy starch can degrade up to 80% in 24 hours, while at a pH=7 it will only degrade 20% over a 24 hour period. This is important to note since pharmaceutical and veterinary medicinal solutions are usually formulated around pH=7.4. Also this shows that the modified starch can be easily hydrolyzed. Erythronic and glyoxylic acids are the principal acidic hydrolysis fragments with minor amounts of glycolic, oxalic and formic acids. This indicates that the C2-C3 dicarboxy polysaccharide structure stays intact (Floor, et al.). FIG. 4 shows the structure of a 50% dicarboxy starch.

These carboxylated cellulosic derivatives can form gels with the addition of divalent cations, such as $Ca^{+2}$. The rate of gelation, the gel strength and the release profile are controlled by percent carboxyl group engineered onto the polymer chain, its position on the polymer chain, and the molecular weight of the polymer chain. Floor (Floor, et al.) has also shown that the calcium complexing properties does not differ with respect to the type of glycosidic bond (i.e. the β-1-4 linkages of cellulose compared to the α 1-4 linkages of starches). It is also important to note that the calcium complexing ability is strongly dependent on the molecular weight in the region $M_w$ $10^4$ to $10^5$ and at least a $M_w$ of $10^5$ is required for superior calcium complexation.

Figure 5:
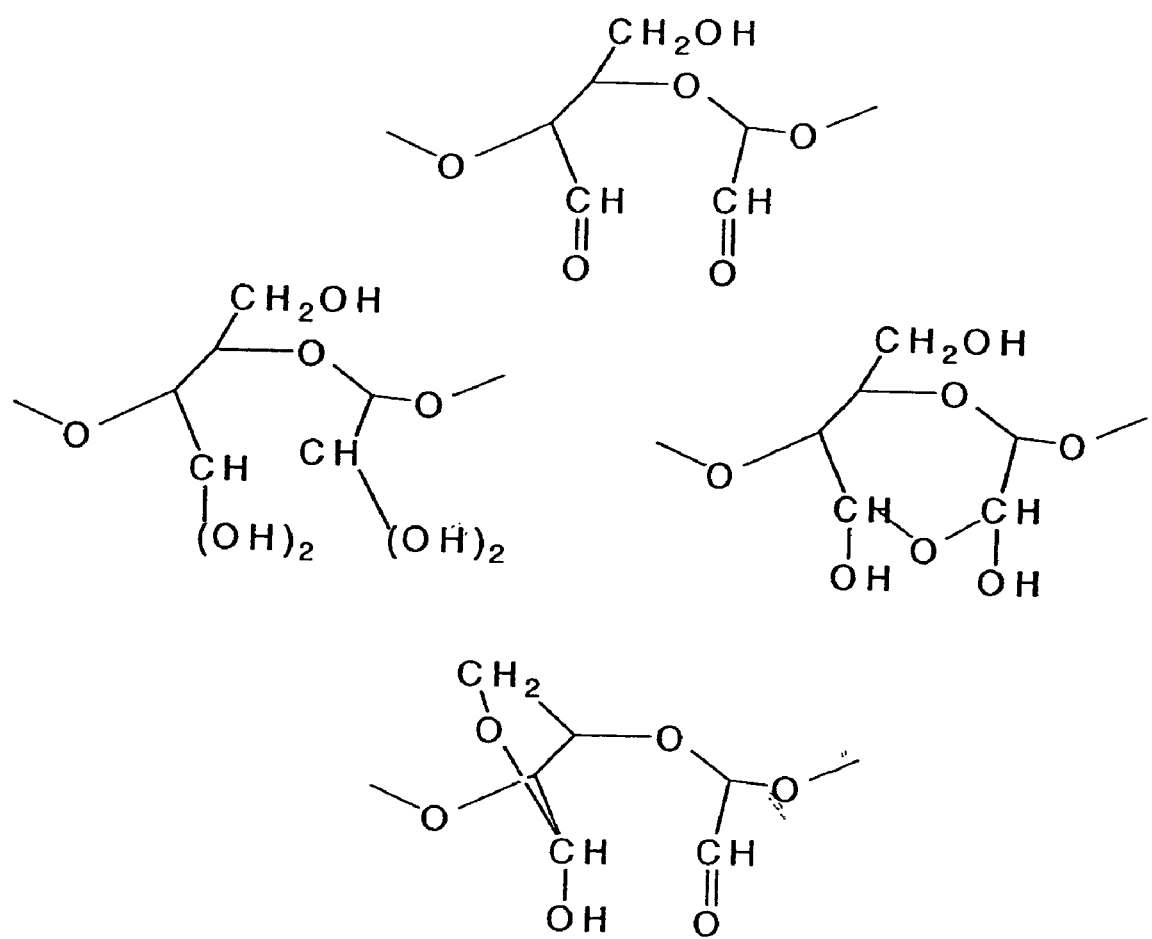
FIG. 5 shows possible structures of periodate-oxidized starch. 1) free aldehyde 2) hydrated aldehyde 3) hemialdol 4) hemiacetal.

The dialdehyde reaction can lead into other formations including a hydrated aldehyde, a hemiacetal, or a hemiadol (Fan, Q.C., D. Lewis et al., Journal of Applied Polymer Science 82:1195-1202 (2001)). The structures of these are shown in FIG. 5.

The periodate reaction is light sensitive and, therefore, care was taken to exclude light. While, some authors (Besemer, A. C., A. E. J. deNooy et al., *Abstracts of Papers of the American Chemical Society* 212 21-Cell (1996); deNooy, A.E.J., A. C. Besemer et al., Zuckerindustrie 122(2) :126-127 (1997); Kim, U. J., S. Kuga et al., *Biomacromolecules* 1(3):488-492 (2000)) suggest running the reaction at room temperature or colder, Narayan (Narayan, R., Conversion of Cellulose and Xylan Into Glycols., Laboratory of Renewable Resources Engineering, Purdue University. NSF Final Report (1983)) reported the reaction could be run at slightly elevated temperatures with little interference from side reactions. For the following Examples, the periodate reaction was run at 40° C. Concentrations were used that were similar to earlier work by the prior art.

It was first proposed (Narayan et al, (1983) that the periodate oxidation of cellulose follow the rate law:

$$r = -\frac{d[P]}{dt} = \frac{K_1[P][C]}{K^{-1} + [P]}$$

This rate law was explained by being consistent with a mechanism involving the formation of an intermediate cellulose-periodate complex, most likely a cellulose-periodate cyclic diester which would then slowly decompose to the final products.

Later an improved explanation of the starch oxidation by periodate was proposed. It has been suggested that the kinetecs follow a $2^{nd}$ order dependence at t=0, then change to another model at approximately t=10 minutes (Veelaert, S., D. Dewit et al., Polymer 35(23):5091-5097 (1994)). This work was conducted using granular potato starch and HPLC for analysis, an improvement method over previous papers which used titration to analyze the dialdehyde formed.

Veelaert et al propose that after 5 to 10 minutes the reaction deviates from second order kinetics because of the polymeric structure of the material and the possibility of hemiacetal or acetal formation. The following two rate laws are defined for free and inhibited anhydroglucose units (an acetal neighbor):

$$\frac{d[X]}{dt} = k_1\mu^2[S_o]([P_o] - [X])$$

$$\frac{d[X]}{dt} = k_2\mu(1-\mu)[S_o]([P_o] - [X])$$

Where [X]=the erythritol concentration at any time

[$S_o$]=the initial starch concentration expressed as total initial anhydroglucose units

[$P_o$]=initial periodate concentration

μ=1-degree of oxidation (1-X/g)

These two equations are combined and from experimental data they observed that $k_2$ was much smaller than $k_1$. The previous formulas then can be simplified into:

$$\frac{d[X]}{dt} = \frac{k_1}{[S_o]}([S_o] - [X])^2([P_o] - [X])$$

Analytical Methods

FTIR

A Perkins Elmer System 2000FTIR was used to characterize samples. The samples were pressed in KBR pellets and run for 16 scans. The wavelength range was 4000 cm$^{-1}$ to 400 cm$^{-1}$.

Titration

Sodium hydroxide was used to titrate against the COOH groups. The sodium hydroxide was standardized against potassium acid phthalate to obtain its normality. It was titrated to an endpoint indicated by phenolphthalein. A concentration of approximately 1-5wt % was used. Because of the viscous nature of the material, the indicator did not react very quickly a false endpoint would show up. The protocol used was if the indicator stayed pink (acid) for 15 minutes without lightening it was considered the endpoint.

ESEM

An environmental scanning electron microscope was used to characterize the structure of the material. The instrument is an ELECTROSCAN 2020 environmental scanning electron microscope. For these samples, there was a beam voltage of 15 kV with an emission current of 49 uA. The water pressure was varied from 2 Torr to 9 Torr.

Dicarboxy Matrix Synthesis and Characterization Oxidation Methods:

First the method of oxidation was examined.

The following three methods were used with the native starch.

TABLE 4

Explanation of Oxidation Methods

| | | Reaction Time | Results |
|---|---|---|---|
| Method 1 | 1-step oxidation with sodium hypochlorite | 24 hours | Completely water soluble product that is extremely hydroscopic in the presence of air. Also yellows when exposed to air. |
| Method 2 | 1-step oxidation with ozone | 6 hours | Non-water soluble product that shows very little carboxyl peaks in IR. |
| Method 3a | 2-step oxidation with sodium m-periodate followed by sodium chlorite | 6 hours + 12-24 hours | Gummy product that is soluble in water. Swells quickly when rewetted. |
| Method 3b | Same as above, except that special care was taken to keep the dialdehyde from drying out in between reactions | 3 hours + 6 hours | Gummy product that is soluble in water Swells quickly when rewetted |

Figure 6:
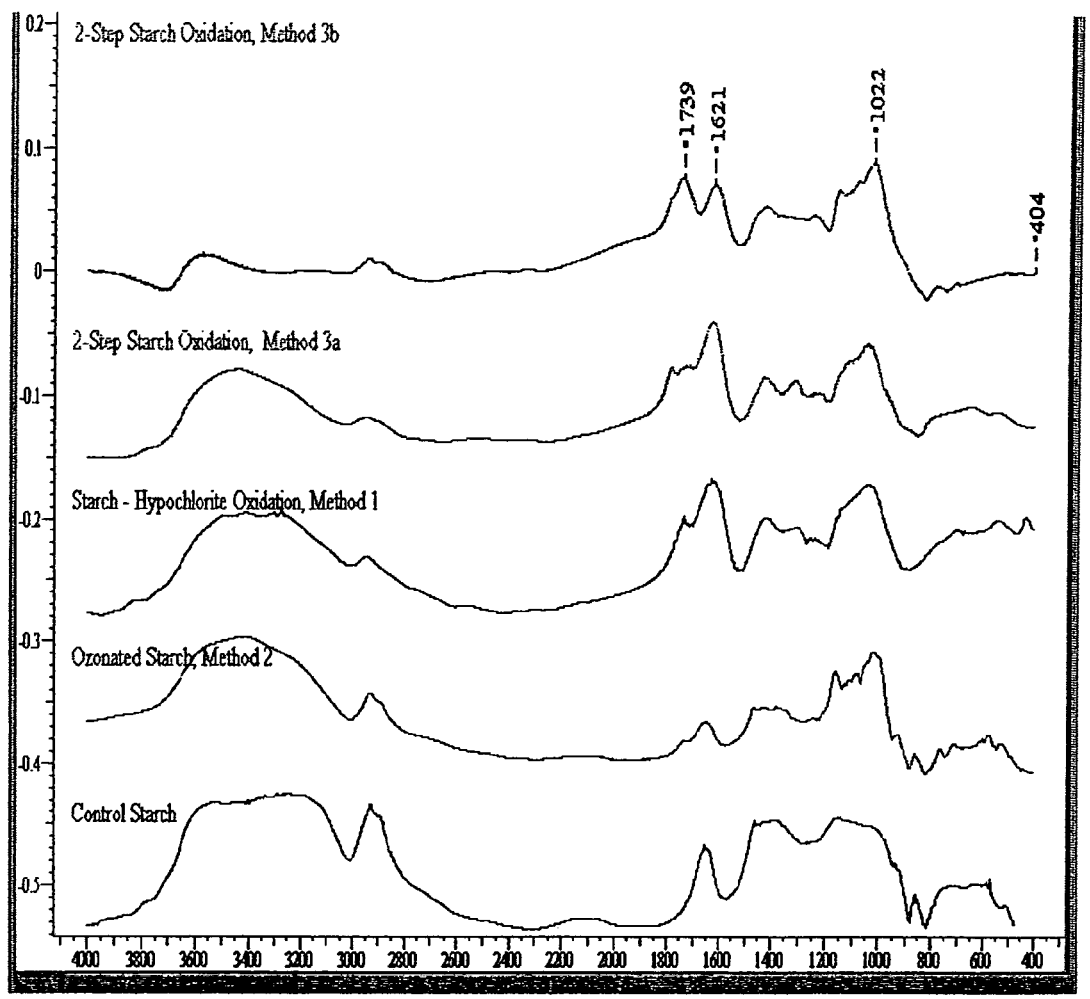
FIG. 6 shows a FTIR Comparison of oxidation methods.
Figure 7:
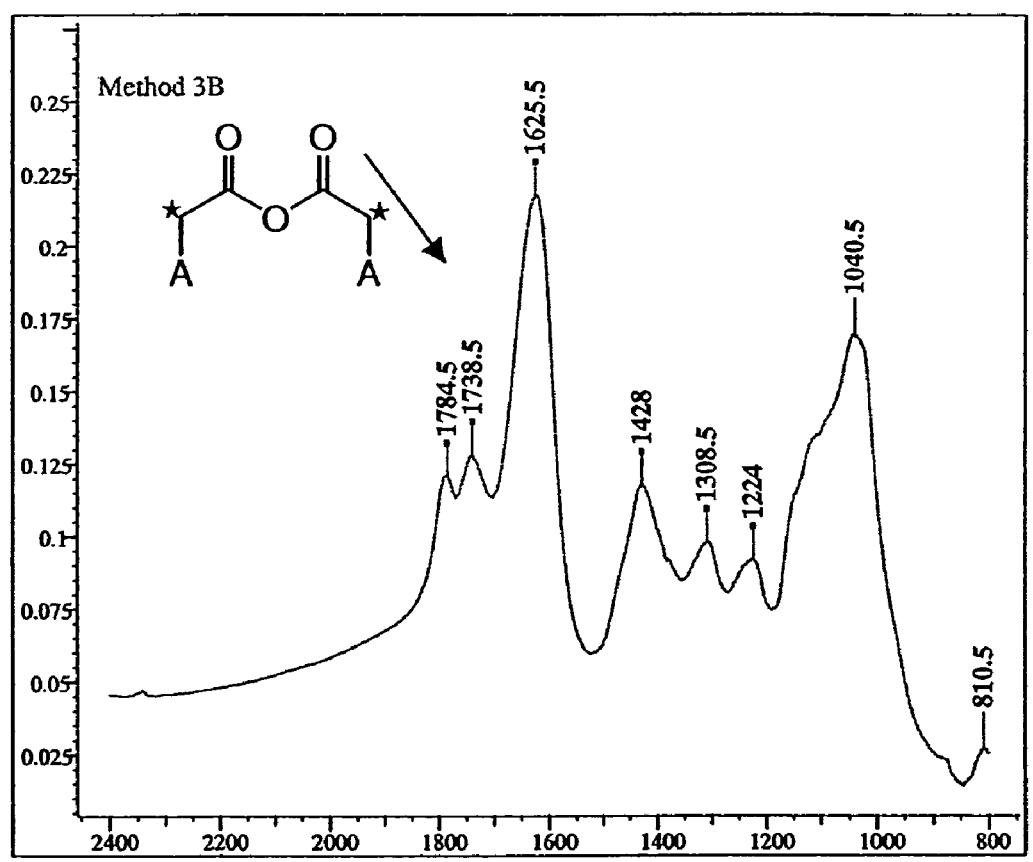
FIG. 7 shows a FTIR of a possible oxidized hemialdol structure.

From the FTIR in FIG. 6, the carbonyl stretch around 1740 cm$^{-1}$ shows that the different methods had different impacts on oxidation. While not quantitative, its comparison can be made by comparing it to the neighboring 1620 cm$^{-1}$ (C—OH) peak. The ozonated starch, so a very slight shoulder around 1740 cm$^{-1}$ indicating that there was some reaction. The hypochlorite method and Method 3a show that there is slightly more carbonyl present but the peak is much smaller than the 1620 cm$^{-1}$. These leads to the possibility that the water solubility of the material may be due to hydrolysis of the starch as opposed to too high a carboxyl presence. As seen in the top peak, there is a high level of carboxyl and the peak is stronger than the 1620 cm$^{-1}$ peak. The difference between the 3a and the 3b method, which in this case had the exact same reactant concentrations, indicates that the structure of the dialdehyde product before the second oxidation plays a very important role in the subsequent oxidation. While this example did not indicate some of the reactions so a presence of an aldol reaction. As seen in FIG. 7, the additional peak at 1784 cm$^{-1}$ indicates the presence of an anhydride which could indicate the presence of the hemi-aldol structure. Specifically a strong anhydride of the structure R—COOCO—R shows a carbonyl stretch at 1790-1740 cm$^{-1}$. This would be consistent of the oxidation of the hemi-aldol structure.

Polysaccharide Choice

Oxidation Method 3a was tried on different saccharides including native corn starch, waxy starch, cellulose, pretreated cellulose, xylans and glucose. The native and waxy starch produced the best results. The cellulose produced similar results but the reaction time was longer and required pretreatment with a strong acid. Because of that the starch was used in subsequent reactions. The following chart summarizes the results of the products.

TABLE 5

The results of the oxidation of different saccharides.

| Material | Comments | Periodate Oxidation Reaction time | Chlorite Oxidation Reaction Time | Results |
|---|---|---|---|---|
| Native Starch | | 6 hours | | Good results, high dicarboxy content, material swells |
| Waxy starch | Waxy pearl 1108 | 6 hours | | Good results, high dicarboxy content, material swells |
| Cellulose | Sigmacell from Sigma-Aldrich | 24 hours | | Only small percentage was oxidized |
| Pretreated Cellulose | Sigmcell pretreated with phosphoric acid and sodium hydroxide | 24 hours | | Good results, high dicarboxy content, material swells |
| Glucose | | 24 hours | | Material was over oxidized |
| Xylans | | 7 hours | | No change in the material |

Titration

Titration with sodium hydroxide was used to measure the amount of carboxyl groups present in the samples. All of the values reported are in terms of carboxyl groups/anhydrogluco ring. For example 100% would indicate that every anhydrogluco ring has one carboxyl group present. Theoretically, the maximum value would be 300% since the C-2, C-3 and C-6 carbon could potentially contain a carboxyl group. Besides actual content, the titration also could be used to quantify the reproducibility of the reaction.

Figure 8:
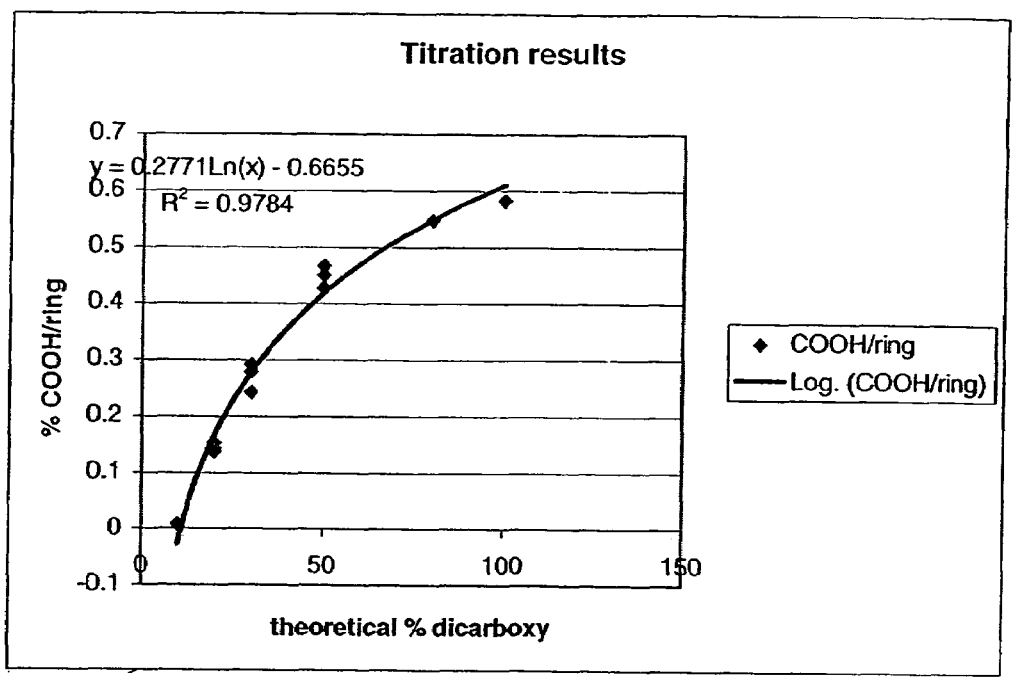
FIG. 8 is a graph showing carboxyl content versus periodate ratio.

Because of the heterogeneity of the material produced using Method 3a for oxidation, titration of those samples was not reproducible. A single sample would have values ranging from 10% -30%. This proved that the material was not being produced in a consistent manner which further confirms that other structures such as hemi-aldols were being formed. Table 4 shows the titration results for the material produced by Method 3b. The standard deviation of titrating a sample in duplicate was from 0.01%-3.1%, which were acceptable values. Also it can be seen from the table that materials produced using the same periodate to starch ratio showed consistent carboxyl content. All of the data presented here were for reactions using 3 hours for the periodate reaction followed by 6 hours for the chlorus acid oxidation with waxy corn starch as the starting material. FIG. 8 graphically shows the relationship between the periodate ratio used and the resulting carboxyl content. A logarithmic dependence can be explained by the fact that as more dialdehyde is the polysaccharide becomes more susceptible to acid hydrolysis breaking the chain into smaller molecular weight chains. These chains are removed during the washing of the material and therefore do not show up in the titration.

TABLE 6

Titration results

| Sample | Periodate ratio % | COOH/ring | Std. Dev. |
|---|---|---|---|
| 44 | 50 | 46.7% | 0.01% |
| 45 | 50 | 45.0% | 0.02% |
| 46 | 30 | 29.1% | 0.03% |
| 47 | 10 | 0.8% | 0.1% |
| 48a | 30 | 27.8% | 2.1% |
| 48b | 30 | 24.2% | 1.8% |
| 49a | 20 | 15.3% | 3.1% |
| 49b | 20 | 12.7% | — |
| 50 | 50 | 42.7% | 1.9% |
| 51a | 20 | 14.3% | 1.5% |
| 51b | 20 | 13.6% | 2.0% |
| 52a | 80 | 54.7% | 1.5% |
| 53a | 100 | 58.2% | 0.0% |

This data deviates from the data presented by Veelaert (Veelaert, S., et al., Polymer 35(23):5091-5097 (1994)), which shows a linear dependence as the stoichiometric amount is increased. This data may be explained by the fact that high amylopectin is being used. This highly branch material may be stericly hindering the oxidation as higher concentrations of periodate are used.

Periodate Oxidation Kinetics Data

Samples were taken during the periodate oxidation of starch and of cellulose at different varying time intervals. The UV spectrophotometer was used to analyze the samples since the periodate has a maximum peak at 223 nm. Data was used from previously obtained periodate data and new data and compared to the model.

A close fitting relationship was found using the Veelaert model. A Runge-Kutta differential equation solver set up on Excel was used to solve for the rate constants. Two separate reactions, one for cellulose and one for starch were compared to the model.

Figure 9:
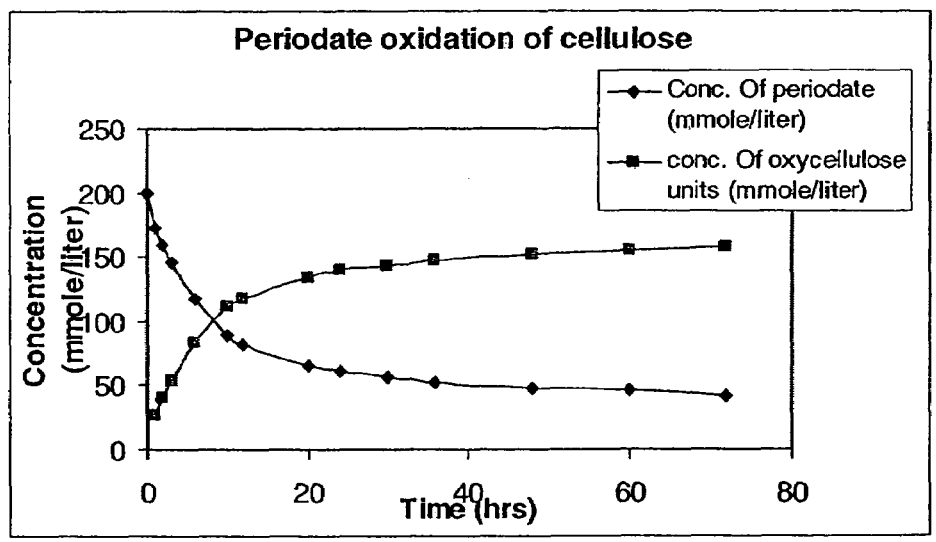
FIG. 9 is a graph showing periodate oxidation of cellulose kinetics.
Figure 10:
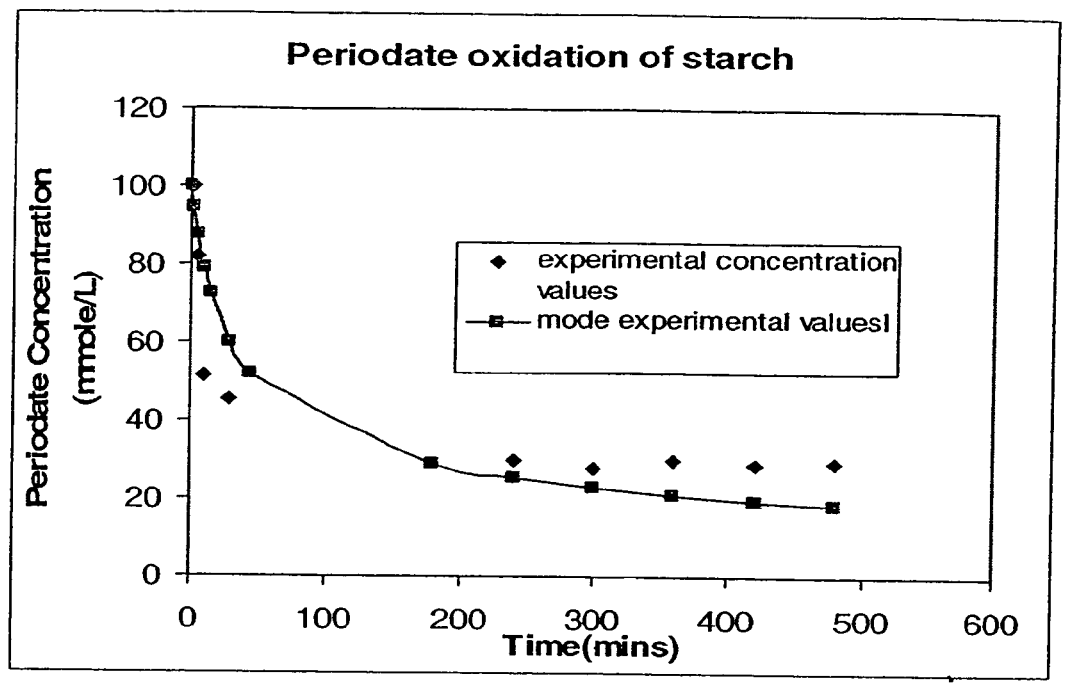
FIG. 10 is a graph showing periodate oxidation of starch kinetics.
Figure 11:
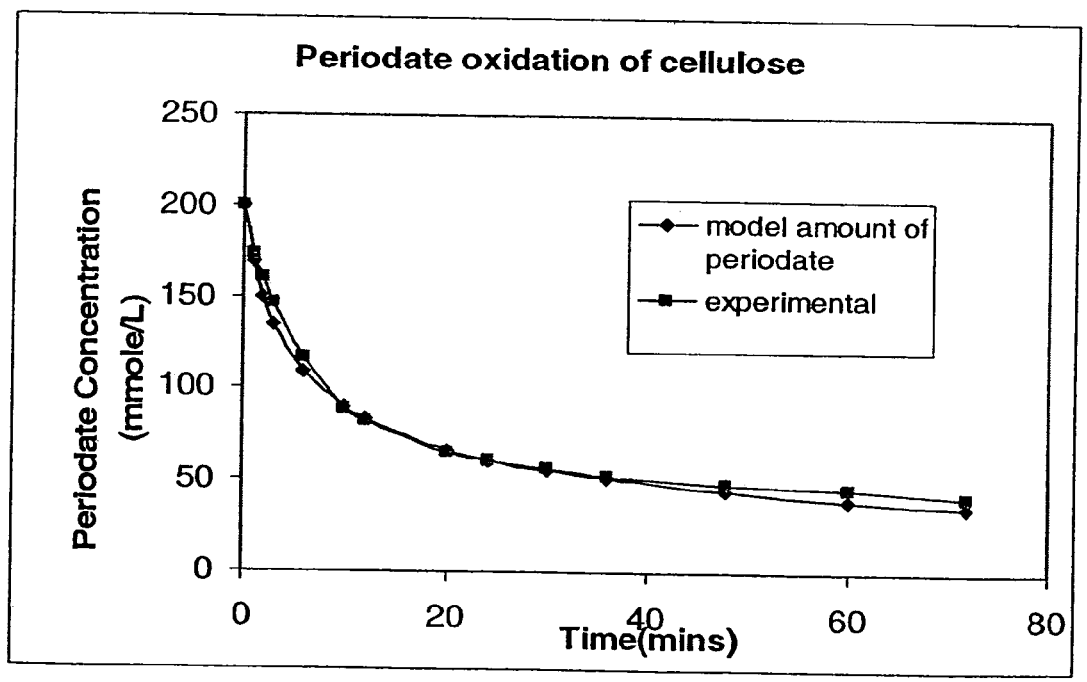
FIG. 11 is a graph showing a comparison of actual and theoretical kinetic data.
Figure 12:
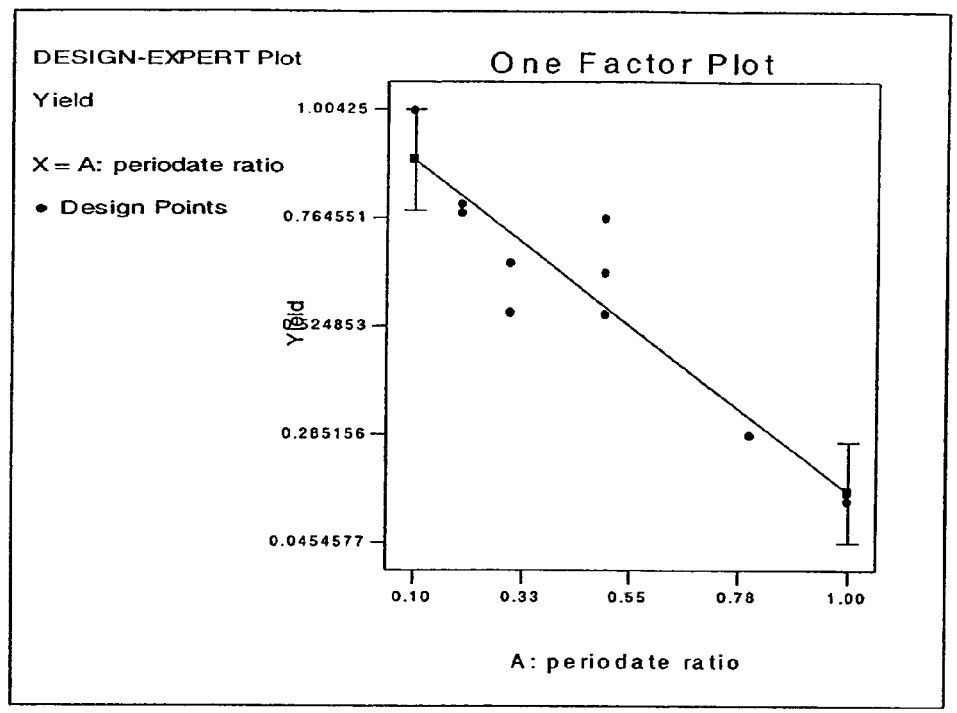
FIG. 12 is a graph showing the relationship between the periodate ratio and the yield.
Figure 13:
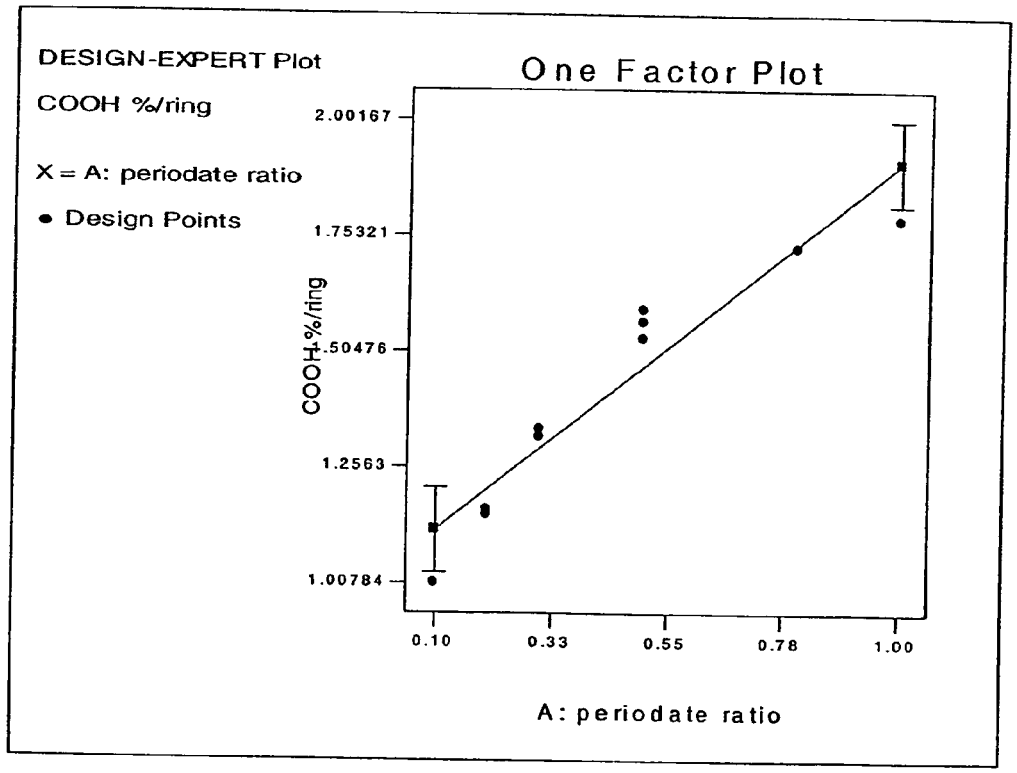
FIG. 13 is a graph showing the relationship between the periodate ratio and the final material acid content.
Figure 14:
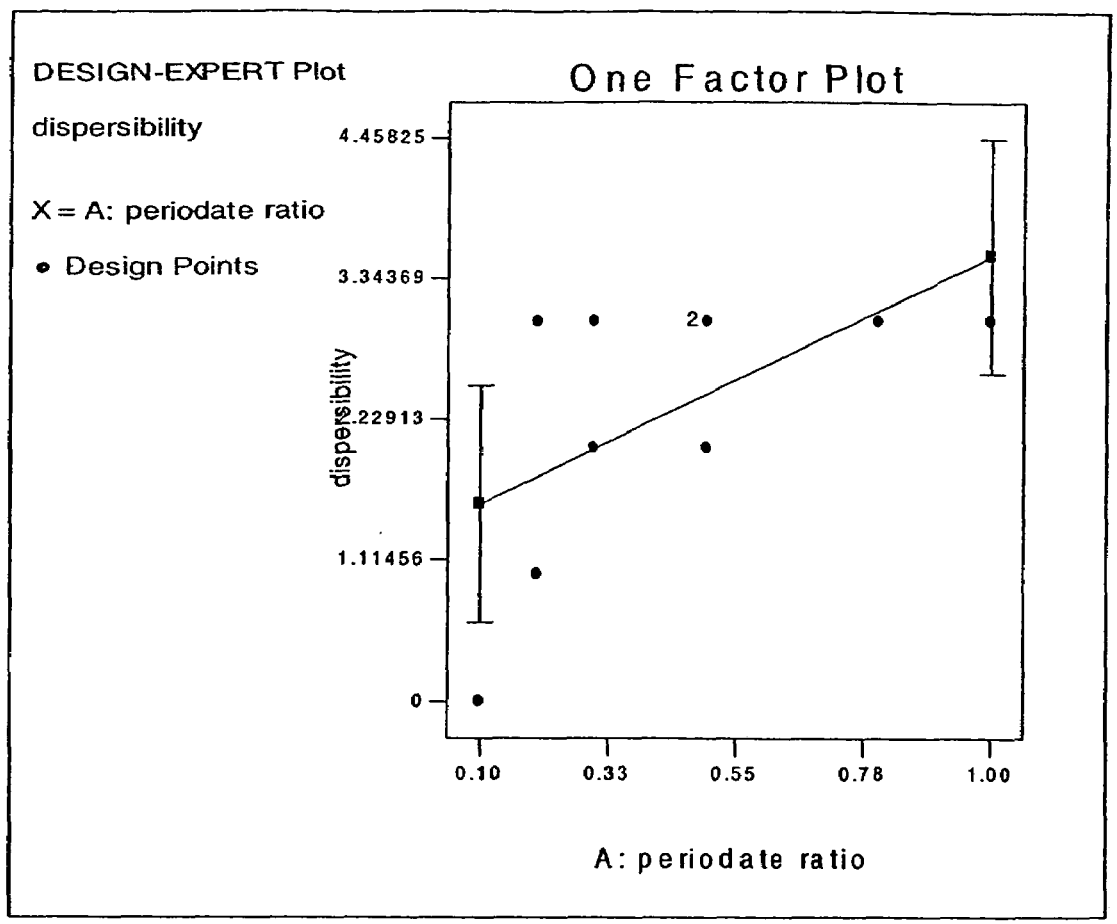
FIG. 14 is a graph showing the relationship between the periodate ratio and the dispersibility of the material.
Figure 15:
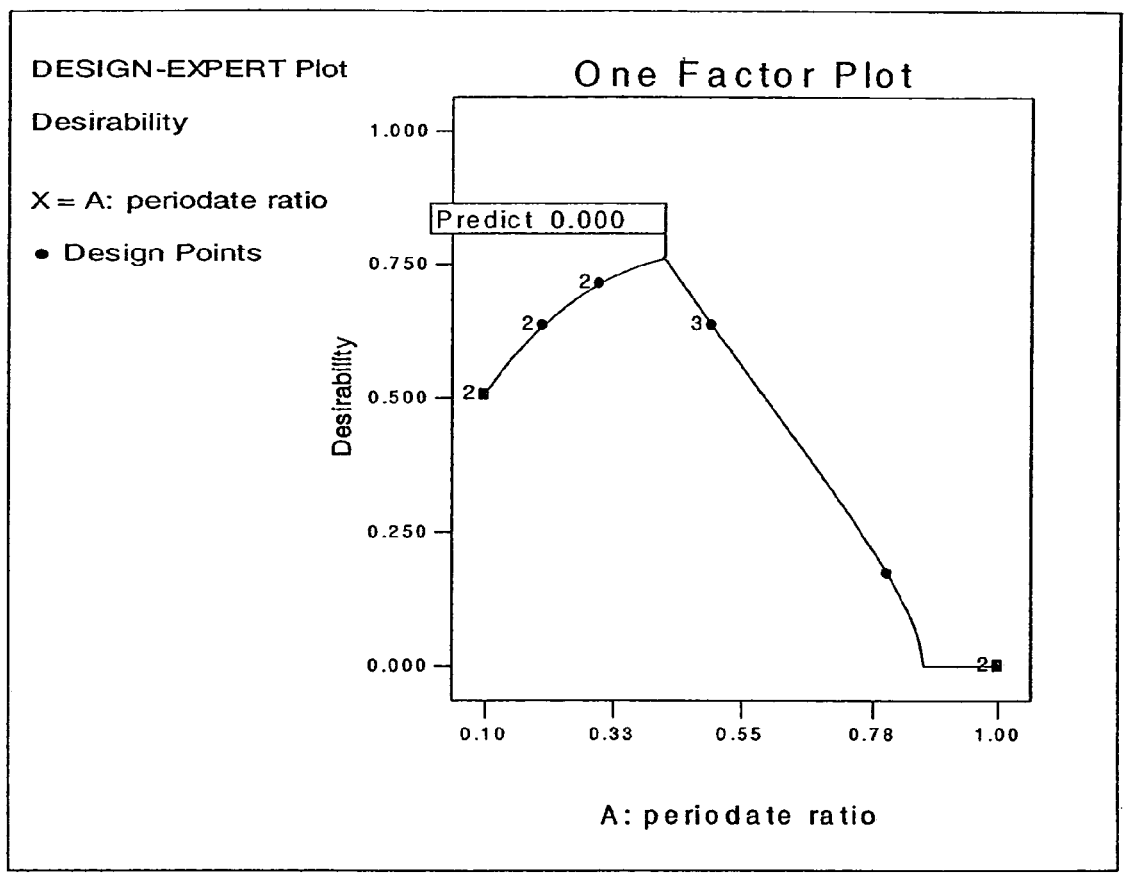
FIG. 15 is a graph showing optimization of the periodate concentration.

As can be seen in FIGS. 9, 10 and 11, the models show a close relationship. The rate constants for each are using the endpoint of three hours and the carboxyl content at that point. This introduces error because the assumption is that the dialdehyde is fully oxidized to carboxyl groups.

TABLE 7

Calculated rate constants for the periodate oxidation of starch

| Sample | % dialdehyde | K(calculated)L/mmole/min |
|---|---|---|
| 47 | 10 | 1.500E-08 |
| 49b | 20 | 1.400E-07 |
| 51a | 20 | 1.250E-07 |
| 46 | 30 | 1.300E-07 |
| 48a | 30 | 1.200E-07 |
| 44 | 50 | 3.492E-07 |

TABLE 7-continued

Calculated rate constants for the periodate oxidation of starch

| Sample | % dialdehyde | K(calculated)L/mmole/min |
|---|---|---|
| 45 | 50 | 3.205E−07 |
| 50 | 50 | 2.800E−07 |
| 52a | 80 | 8.300E−07 |
| 53a | 100 | 1.350E−06 |

Design of Experiments

Stat-Ease software, Design-Expert 5.0 was used to create a design of experiments to see how the initial periodate ratio affected the product. This was used to optimize the reaction to predict the most desirable product. The final results of this were used as the case that was scaled up as set forth hereinafter. Acid content, overall reaction yield and dispersibility were used to qualify the product. The titration results were used for the acid content. Because of the logarithmic relationship shown in FIGS. 12 to 15, the exponential values of the carboxyl content were used. The yield was calculated by looking at the percentage of the polymeric material left at the end of the reaction compared to the theoretical amount that could be produced and dispersibility was rated on a scale of 0 to 3. On this scale a 3 indicated that within 10 minutes of adding the material to water it appeared completely dispersed, a 2 indicated that in that time frame the majority of the material was swollen and dispersed, a 1 indicated that a majority of the material was not dispersed but at the least the material had swollen considerably and a 0 indicated that there was no visible hydration of the material within the 10 minute timeframe. This is an important factor to consider for manufacturing and formulating of a final product and to ensure that the drug can be uniformly distributed in the matrix. Carboxyl contents and reaction yield showed a statistically significant relationship to the periodate ratio used and the dispersibility show a relationship with a $p=0.0761$.

Response: Yield
ANOVA for Response Surface Linear Model
Analysis of variance table [Partial sum of squares]

| Source | Sum of Square | DF | Mean Square | F Value | Prob > F |
|---|---|---|---|---|---|
| Model | 0.48 | 1 | 0.48 | 40.98 | 0.0002 |
| Significant A | 0.48 | 1 | 0.48 | 40.98 | 0.0002 |
| Residual | 0.094 | 8 | 0.012 | | |
| Lack of Fit | 0.066 | 4 | 0.016 | 2.30 | 0.2204 not significant |
| Pure Error | 0.029 | 4 | 7.166E−003 | | |
| Cor Total | 0.58 | 9 | | | |

The Model F-value of 40.98 implies the model is significant. There is only a 0.02% chance that a "Model F-Value" this large could occur due to noise.

Values of "Prob>F" less than 0.0500 indicate model terms are significant. In this case A are significant model terms.

Values greater than 0.1000 indicate the model terms are not significant.

If there are many insignificant model terms (not counting those required to support hierarchy), model reduction may improve your model.

Final Equation: Yield=+0.97444−0.81743 *periodate ratio

Response: COOH %/ring
ANOVA for Response Surface Linear Model
Analysis of variance table [Partial sum of squares]

| Source | Sum of Square | DF | Mean Square | F Value | Prob > F |
|---|---|---|---|---|---|
| Model | 0.56 | 1 | 0.56 | 70.70 | <0.0001 |
| Significant A | 0.56 | 1 | 0.56 | 70.70 | <0.0001 |
| Residual | 0.063 | 8 | 7.864E−003 | | |
| Lack of Fit | 0.061 | 4 | 0.015 | 28.71 | 0.0033 significant |
| Pure Error | 2.117E−003 | 4 | 5.293E−004 | | |
| Cor Total | 0.62 | 9 | | | |

The Model F-value of 70.70 implies the model is significant.

There is only a 0.01% chance that a "Model F-Value" this large could occur due to noise.

Values of "Prob>F" less than 0.0500 indicate model terms are significant. In this case A are significant model terms. Values greater than 0.1000 indicate the model terms are not significant.

Final Equation: COOH %/ring=+1.03430+0.87633 *periodate ratio

Response: Dispersibility
ANOVA for Response Surface Linear Model
Analysis of variance table [Partial sum of squares]

| Source | Sum of Square | DF | Mean Square | F Value | Prob > F |
|---|---|---|---|---|---|
| Model | 3.45 | 1 | 3.45 | 4.16 | 0.0761 |
| Significant A | 3.45 | 1 | 3.45 | 4.15 | 0.0761 |
| Residual | 6.65 | 8 | 0.83 | | |
| Lack of Fit | 3.49 | 4 | 0.87 | 1.10 | 0.4641 not significant |
| Pure Error | 3.17 | 4 | 0.79 | | |
| Cor Total | 10.10 | 9 | | | |

The Model F-value of 4.15 implies there is a 7.61% chance that a "Model F-Value" this large could occur due to noise. Values of "Prob>F" less than 0.0500 indicate model terms are significant. In this case there are no significant model terms. Values greater than 0.1000 indicate the model terms are not significant. If there are many insignificant model terms (not counting those required to support hierarchy), model reduction may improve your model.

Final Equation: dispersibility=+1.33978+2.18232 *periodate ratio

Optimization Results

The following constraints were set to find the optimal periodate ratio used.

Constraints

| Name | Goal | Lower Limit | Upper Limit | Importance |
|---|---|---|---|---|
| Periodate ratio | Is in range | 0.1 | 1 | 3 |
| Yield | Maximize | 0.136 | 1 | 3 |
| COOH %/ring | Is target = 1.398 | 1.007 | 1.789 | 3 |

| Solution Periodate ratio | Yield | COOH %/ring |
|---|---|---|
| 0.42 | 0.634683 | 1.39854 |

This design of experiments can be expanded to incorporate the release data and calculated diffusion coefficients to develop a predictive model with reactant molarity as the input and diffusion coefficients as the output.

ESEM

Figure 16A:
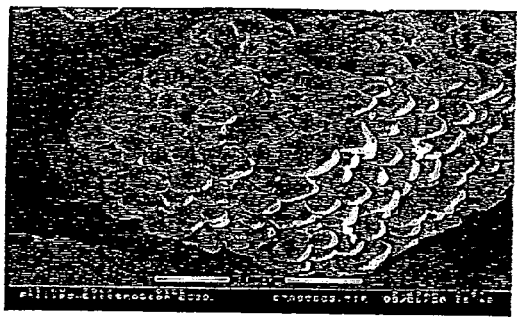
FIGS. 16A to 16E show ESEM (scanning electron microscope) images of starch (FIGS. 16A to 16C), air dried dicarboxy starch (FIG. 16D) and hydrated dicarboxy starch (FIG. 16E).
Figure 16B:
Figure 16D:
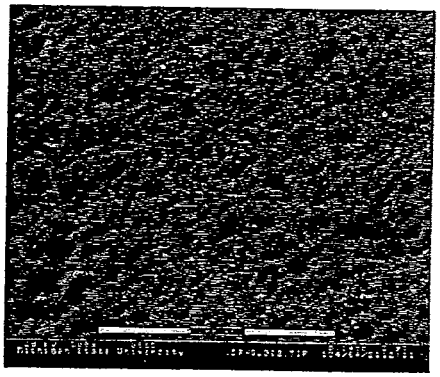
Figure 16C:
Figure 16E:
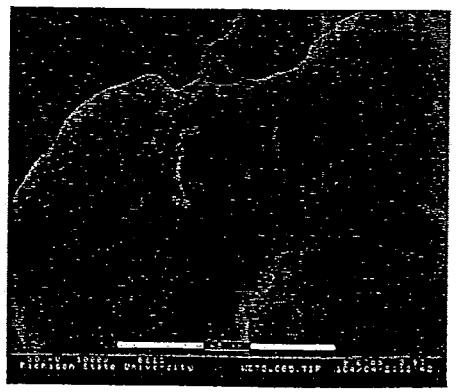

As seen in the ESEM images (see FIGS. 16A to 16E) there is a difference between native starch and the dicarboxy starch. It can be observed that the oxidation process destroys the granular structure of the starch (FIG. 16A), releasing the amylase and amylopectin from the structure creating a smooth and flexible material (FIG. 16D). The ESEM is run under vacuum so it is impossible to observe the hydrated structure. However, the swelling and subsequent dehydration of the material can be observed while the material is first wetted and the vacuum chamber comes to equilibrium (FIG. 16E).

Synthesis of Grafted Dicarboxy Starch and Characterization

The engineered dicarboxylate material can be characterized by FTIR and titration methods to analyze the amount of added carboxylate groups. The dicarboxy starch is water dispersible and shows drug release profiles consistent of hydrogel matrices. This makes it suitable for a drug delivery system. Using the diffusion model presented, the modified starch can be engineered to have exhibit desired diffusion properties. This modified starch has the potential to be used in a variety of drug delivery applications including topical and depot ocular, medicated wound dressing. The modified starch as a good ability to adhere to biological surfaces. The mucoadhesive can be used for mucoadhesive applications such as nasal drug delivery.

Kinetic considerations and scale up

In FIG. 17, a large-scale batch process for the production of the dicarboxy starch is described.

| | |
|---|---|
| Formulated product required/annually | 200000 kg |
| Assume 10,000,000 bottles & 20 ml each | |
| Amount of dicarboxy starch needed/annually | 2000 kg |
| # of batch runs annually | 50 |
| Amount/barch needed for 42% dialdehyde | 40 kg |
| Yield | 63.47% |
| Reactants/batch | |
| Starch | 60.9 kg |
| Sodium m-periodate | 33.8 kg |
| Water | 6282.4 kg |
| Acetic Acid | 13.6 kg |
| Hydrogen Peroxide | 45.1 kg |
| Na-EDTA | 0.8 kg |
| Sodium Chlorite | 42.5 kg |

Reactor 1 is a 500 gallon stainless steel jacketed reactor. Water would be used to heat the reactor to 40° C. The second reactor is a stainless steel 1250 gallon reactor. Chlorine byproduct is controlled and quenched accordingly. The ethanol/water washwater is recycled using a basic distillation column.

A suitable filter that ionically repels the material or at least, not attract it. The iodate can be reoxidized electrolytically to periodate or can be oxidized to paraperiodate using sodium hypochlorite which then will release the metaperiodate ion.

Reduction of the aldehyde groups to —OH groups provides hydroxyl moieties in addition to carboxylic moieties.

It is intended that the foregoing description be only illustrative of the present invention and that the present invention be limited only by the hereinafter appended claims.

We claim:

1. A chemically modified polysaccharide (CMP) comprising: a random copolymer comprising:
   (a) starch-derived or cellulose-derived saccharide rings having $C_2$ and $C_3$ carbon positions and a bond therebetween, the saccharide rings being linked with
   (b) ring-opened starch-derived or cellulose-derived saccharide units at the bond between the $C_2$ and $C_3$ carbon positions; wherein:
      (i) at least some of the ring-opened $C_2$ and $C_3$ carbon positions are carboxylic acid moieties, water dispersible salts thereof, or combinations thereof directly attached thereto;
      (ii) at least some of the ring-opened $C_2$ and $C_3$ carbon positions contain hydroxyl groups; and,
      (iii) the CMP is water dispersible to form a clear solution.

2. A pharmaceutical composition which comprises:
   (a) a medicament; and
   (b) a chemically modified polysaccharide (CMP) comprising a random copolymer comprising: starch-derived or cellulose-derived sacccharide rings having $C_2$ and $C_3$ carbon positions and a bond therebetween, the saccharide rings being linked with ring-opened starch-derived or cellulose-derived saccharide units at the bond between the $C_2$ and $C_3$ carbon positions, wherein:
      (i) at least some of the ring-opened $C_2$ and $C_3$ carbon positions contain carboxylic acid moieties, water dispersible salts thereof, or combinations thereof;
      (ii) at least some of the ring-opened $C_2$ and $C_3$ carbon positions contain hydroxyl groups; and
      (iii) the CMP is water dispersible to form a clear solution as a time-release adjuvant for the medicament.

3. The composition of claim 2 wherein the medicament is to be used for treatment of tissue of a living animal.

4. The composition of claim 2 wherein the medicament is to be used for treatment of tissue of a living human.

5. A chemically modified polysaccharide (CMP) comprising: a random copolymer comprising:
   (a) saccharide rings having $C_2$ and $C_3$ carbon positions and a bond therebetween, the saccharide rings being linked with
   (b) ring-opened saccharide units at the bond between the $C_2$ and $C_3$ carbon positions; wherein:
      (i) the saccharide rings are represented by Formula I;

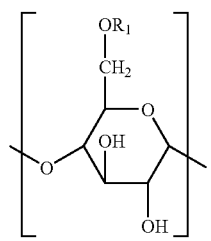

Formula I (ii) the ring-opened saccharide units are represented by Formula II;

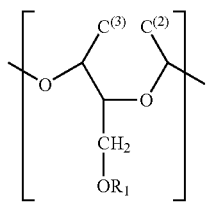

Formula II (iii) $R_1$ is H or —COOR where R is alkyl or aryl;
(iv) $C^{(2)}$ and $C^{(3)}$ are independently selected from the group consisting of —CH$_2$OH, —COOH, water-dispersible salts thereof, and combinations thereof;
(v) at least some of $C^{(2)}$, $C^{(3)}$, or combinations thereof are —COOH, water-dispersible salts thereof, or combinations thereof;
(vi) at least some of $C^{(2)}$, $C^{(3)}$, or combinations thereof are —CH$_2$OH; and,
(vii) the CMP is water dispersible to form a clear solution.

6. A chemically modified polysaccharide (CMP) comprising: a random copolymer comprising:
(a) saccharide rings having $C_2$ and $C_3$ carbon positions and a bond therebetween, the saccharide rings being linked with
(b) ring-opened saccharide units at the band between the $C_2$ and $C_3$ carbon positions; wherein:

(i) the CMP is represented by Formula III;

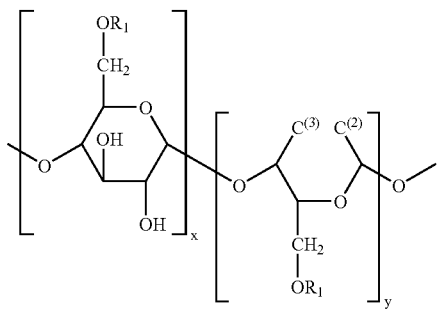

Formula II (ii) the mole fraction Y of ring-opened saccharide units in the random copolymer ranges from 0.1 to 0.9;
(iii) $R_1$ is H or —COOR where R is alkyl or aryl;
(iv) $C^{(2)}$ and $C^{(3)}$ are independently selected from the group consisting of —CH$_2$OH, —COOR$_2$, and combinations thereof, where $R_2$ is H, an alkyl or an aryl group containing 1 to 12 carbon atoms;
(v) at least some of $C^{(2)}$, $C^{(3)}$ or combinations thereof are —COOR$_2$;
(vi) at least some of $C^{(2)}$, $C^{(3)}$, or combinations thereof are —CH$_2$OH; and,
(vii) the CMP is water dispersible to form a clear solution.

* * * * *

UNITED STATES PATENT AND TRADEMARK OFFICE
CERTIFICATE OF CORRECTION

PATENT NO.        : 7,456,265 B2
APPLICATION NO.   : 11/125865
DATED             : November 25, 2008
INVENTOR(S)       : Ramani Narayan and Laura M. Fisher Page 1 of 1

It is certified that error appears in the above-identified patent and that said Letters Patent is hereby corrected as shown below:

Column 10, line 33, "Significant A" should be --Not Significant A--.

Column 14, line 5, "Formula II" should be --Formula III--.

Signed and Sealed this

Sixteenth Day of June, 2009

JOHN DOLL
*Acting Director of the United States Patent and Trademark Office*